(12) United States Patent
Toury et al.

(10) Patent No.: US 7,710,573 B2
(45) Date of Patent: *May 4, 2010

(54) DEVICE AND METHOD FOR THE NON-INVASIVE DETECTION AND MEASUREMENT OF THE PROPERTIES OF A MEDIUM

(75) Inventors: Timothée Pol Jean Toury, Tournes (FR); Joseph Zyss, Sceaux (FR)

(73) Assignees: Ecole Normale Superieure de Cachan, Cachan (FR); Centre National de la Recherche Scientifique—CNRS, Paris (FR)

( * ) Notice: Subject to any disclaimer, the term of this patent is extended or adjusted under 35 U.S.C. 154(b) by 805 days.

This patent is subject to a terminal disclaimer.

(21) Appl. No.: 10/568,250

(22) PCT Filed: Aug. 18, 2004

(86) PCT No.: PCT/FR2004/002157

§ 371 (c)(1),
(2), (4) Date: Nov. 21, 2006

(87) PCT Pub. No.: WO2005/022128

PCT Pub. Date: Mar. 10, 2005

(65) Prior Publication Data
US 2007/0070352 A1 Mar. 29, 2007

(30) Foreign Application Priority Data
Aug. 22, 2003 (FR) .................................. 03 10116

(51) Int. Cl.
*G01B 9/02* (2006.01)

(52) U.S. Cl. ..................................................... 356/450
(58) Field of Classification Search ................. 356/35.5, 356/450, 484, 491; 324/76.36, 76.37
See application file for complete search history.

(56) References Cited

U.S. PATENT DOCUMENTS

| 5,394,098 A | | 2/1995 | Meyrueix et al. |
| 6,072,179 A | * | 6/2000 | Paniccia et al. ......... 250/341.4 |
| 6,271,671 B1 | * | 8/2001 | Charles et al. ............ 324/753 |

(Continued)

FOREIGN PATENT DOCUMENTS

EP 0 864 872 A2 9/1998

OTHER PUBLICATIONS

D. Leiner, et al., "Real-time" phase microscopy using a phase-lock interferometer, Re. Sci. Instrum, XP002315966, pp. 1702-1705, Dec. 1, 1978.

(Continued)

*Primary Examiner*—Michael A Lyons
(74) *Attorney, Agent, or Firm*—Miller, Mattias & Hull

(57) ABSTRACT

The invention relates to a device useful for non-invasive detection of the properties of a medium by means of interferometry. The device comprises an optical source which is used for illuminating a zone of the medium that is to be probed with a light beam, and an interferometer for splitting the light beam into a reference beam and a probe beam. The interferometer has a cutoff frequency for the automatic control of respective path lengths of the reference beam and of the probe beam. The device also comprises scanning means which, together with the probe beam, are used to scan the zone to be probed at an image acquisition frequency greater than the cutoff frequency.

27 Claims, 3 Drawing Sheets

U.S. PATENT DOCUMENTS 6,587,258 B1 * 7/2003 Kane .......................... 359/328
6,803,777 B2 * 10/2004 Pfaff et al. .................. 324/752
7,206,078 B2 * 4/2007 Pfaff et al. .................. 356/517
7,450,237 B2 * 11/2008 Zyss et al. .................. 356/450

2002/0003628 A1 1/2002 James et al.

OTHER PUBLICATIONS

International Search Report PCT/FR2004/002157; report dated Feb. 28, 2005.

* cited by examiner

10 μm *(indicative scale)*
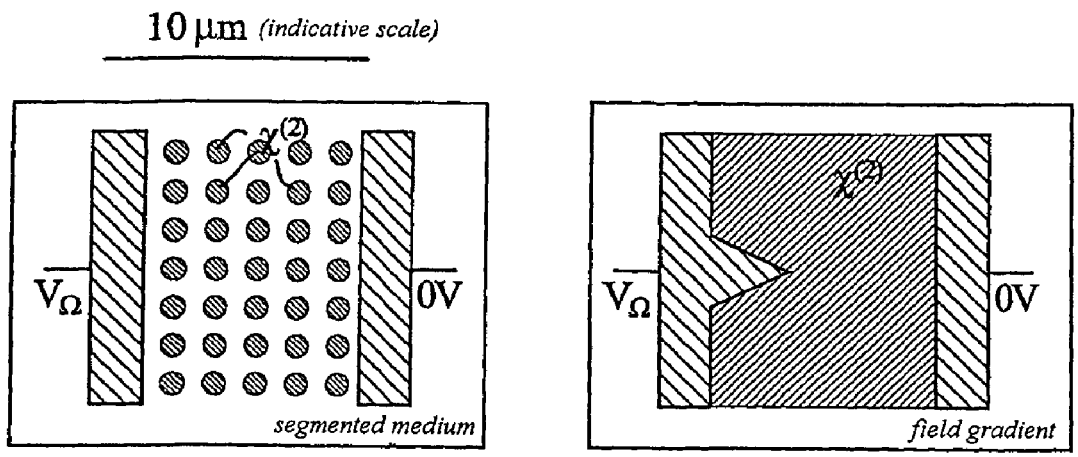
FIG. 5a *segmented medium*
FIG. 5b *field gradient*
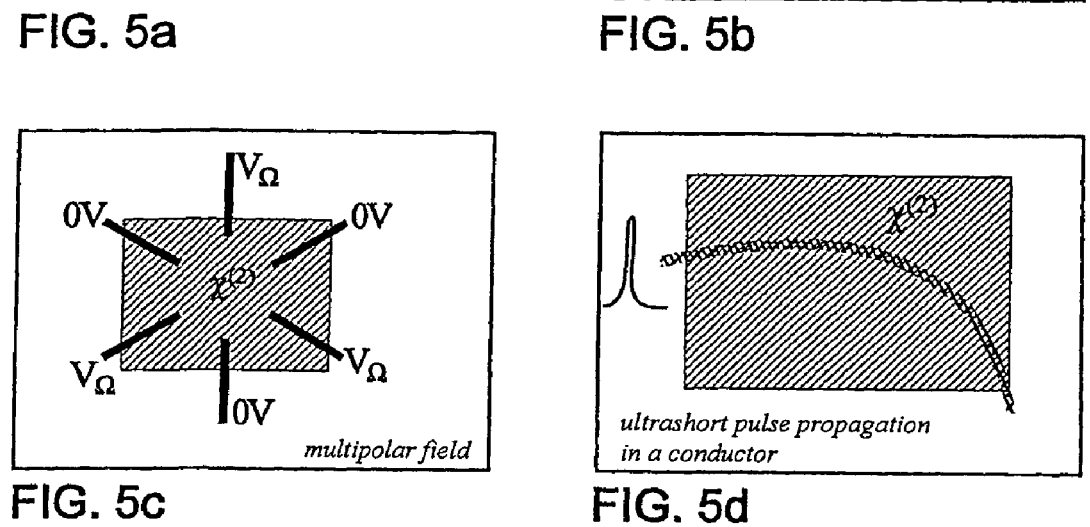
FIG. 5c *multipolar field*
FIG. 5d *ultrashort pulse propagation in a conductor*
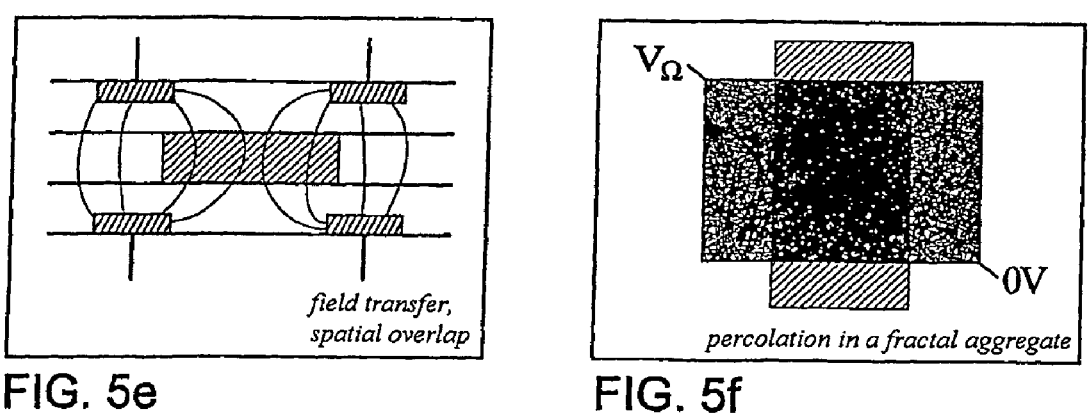
FIG. 5e *field transfer, spatial overlap*
FIG. 5f *percolation in a fractal aggregate*

DEVICE AND METHOD FOR THE NON-INVASIVE DETECTION AND MEASUREMENT OF THE PROPERTIES OF A MEDIUM

FIELD OF THE INVENTION

The present invention relates to devices and methods for a noninvasive detection and measurement of the optical properties and electric fields of a medium.

More particularly, the invention relates to a device for the noninvasive detection of the properties of a medium by interferometry, this device comprising:
  an optical source for illuminating at least one region of the medium to be probed, with a light beam whose path defines an optical axis;
  means for measuring the variations in the phase of the light beam during its passage through the region to be probed, these measurement means
    comprising an interferometer for splitting the light beam into a reference beam and a probe beam, in this interferometer the servocontrol of the respective path lengths of the reference beam and of the probe beam being active up to a cutoff frequency $f_c$ and
    having a signal sampling frequency $f_a$.

BACKGROUND OF THE INVENTION

Document U.S. Pat. No. 5,394,098 describes an example of such a device used for testing optoelectronic components, using an optical source consisting of a laser. More precisely, electric fields are measured in the optoelectronic components by means of a layer of material constituting an optically active medium covering at least part of the component that it is desired to test.

In the present document, the expression "optically active medium" is understood to mean a medium having electrooptic properties and more particularly a medium having a linear electrooptic effect (also called the Pockels effect), or a quadratic electrooptic effect, the manifestation threshold of which is however higher than in the linear case, while still remaining compatible with the use of short-pulse power lasers.

This type of device does however have the drawback of allowing measurements only at a signal sampling frequency $f_a$ above the cutoff frequency $f_c$. This type of device cannot be used in particular for detection of electric fields within the volume of biological media, since the variations in refractive index that are due to electric fields in biological systems essentially take place at frequencies below 1 kHz, whereas the frequency $f_c$ must be a few kHz in order to eliminate external (thermal, mechanical, acoustic, etc.) noise.

It is an object of the present invention in particular to alleviate this drawback.

SUMMARY OF THE INVENTION

For this purpose, the invention provides a device for the noninvasive detection of the properties of a medium by interferometry, which device, apart from the features already mentioned, includes scanning means suitable for scanning, with the probe beam, the region to be probed and a reference region with an image acquisition frequency f for the images recorded by the means for measuring the variations in the phase of the light beam above the cutoff frequency $f_c$.

Thus, a modulation of the frequency of variation of the signal corresponding to the observed electrooptic phenomenon is obtained at a higher frequency f and advantageously a frequency higher than the cutoff frequency $f_c$ for the (low-pass) servocontrol of the respective path lengths of the reference beam and the probe beam.

We also note that the reference region may have a minimum size of a pixel.

In the embodiments of the invention, there may optionally also be one or other of the following arrangements:
  the scanning means scan the region to be probed and the reference region along a first direction in space at a frequency $f_x$ and along a second direction in space at a frequency $f_y$, in order to form an image of n pixels along the first direction and m pixels along the second direction, the frequencies $f_x$ and $f_y$ being chosen such that $f_x=f_y/n$ and $f_y=f_a/m$, $f_x$ and $f_y$ being greater than $f_c$; in fact, these first and second directions in space are perpendicular to the optical axis;
  the means for measuring the variations in the phase of the light beam comprise a confocal microscope in which the region to be probed is placed in a manner suitable for forming an image of a plane of the region to be probed. Thus, thanks to the confocal microscope, a three-dimensional spatial resolution may be obtained. It is then possible to probe the volume of the medium. This arrangement allows a medium to be probed without particular preparation if the medium is endowed with electrooptic properties. The spatial resolution of the electric field measurement is limited only by the optics used;
  it includes means for moving the medium, along the three directions in space, in the probe beam;
  the scanning means comprise four acoustooptic deflectors, two for deflecting the light beam, upstream of the confocal microscope, each in one of the first and second directions in space respectively, and two for rectifying the light beam, each in one of the first and second directions in space respectively, downstream of the confocal microscope;
  at least one acoustooptic deflector, downstream of the confocal microscope is set so as to make the 0th-order of the light beam inclined to the optical axis and to retain the paraxial 1st-order. Thus, the $0^{th}$-order of the beam leaves the optical axis and one of the $1^{st}$-orders of the beam, output by the first deflectors, has a mean position on the optical axis. If the intensity of the 0th-order of the beam is nonzero, the corresponding part of the beam leaves the optical axis and reaches neither the region to be probed nor the beam photodetection means. Optionally, a Galileo telescope allows the angle between the 1st-order and the optical axis to be increased; and
  it includes, upstream of the confocal microscope, means for controlling the polarization of the probe beam incident on the region to be probed.

Many other types of scanning other than that mentioned above may be envisioned. Just a few of them may be mentioned:
  rectangular scanning: the scanning is carried out over a region of interest, comprising the region to be probed and the reference region, which is smaller than the area effectively accessible. This type of scanning is in particular useful if the region to be probed is small—this may then be profitably used for scanning at a higher frequency with the same resolution, or for increasing the resolution by constricting the pixels or any intermediate solution;
  multi-rectangle scanning: the scanning is carried out over a region corresponding to a set of rectangles, such as those described in the previous paragraph. The reference region may be a single region, whereas the various regions to be probed correspond to different rectangles. This may be useful if the region to be probed cannot be covered by a single rectangle;

scanning over areas of various shapes: the scanning is carried out over areas that are circular, elliptical, triangular, etc. or over a composition of these areas;

scanning over complex surfaces: the scanning is carried out over surfaces with complex shapes, as the application requires, for example for studying all or part of an optoelectronic component or of a biological system (neuron, membrane, artificial membrane, for example of the Langmuir-Blodgett film type, etc.); and parameterized scanning: the scanning is carried out along paths with the coordinates x and y parameterized as follows:

$$x=\cos(w.n.t)$$

$$y=\cos(w.n.m.t)$$

in which n and m are substantially the numbers of pixels corresponding to an acquisition period along the x and y coordinates respectively. This type of scanning makes it possible to approach the limits of the acoustooptic modulators as closely as possible. Of course, it is also possible to keep this parameterization only on one of the two coordinates.

It should be noted that the construction of the system for controlling these various types of scanning are known to those skilled in the art.

According to another aspect, the invention relates to a method of using the device according to the invention. In particular, this is a method of noninvasively detecting the properties of a medium by interferometry, in which:

at least one region of the medium to be probed is illuminated with an optical source that generates a light beam, the path of which defines an optical axis;

an interferometer is used to split the light beam into a reference beam and a probe beam and to measure the phase shift between the reference beam and the probe beam after the latter has passed through the region to be probed;

the respective path lengths of the reference beam and the probe beam are servocontrolled by photodetection means; and images corresponding to the measurement of the phase shift at various points in the region to be probed are acquired, with the photodetection means, at a signal sampling frequency $f_a$ above the cutoff frequency $f_c$ for servocontrolling the respective path lengths of the reference beam and the probe beam, wherein the region to be probed and a reference region are scanned with the probe beam at an image acquisition frequency f for images recorded by the means for measuring the variations in the phase of the light beam above the cutoff frequency $f_c$.

In some of the ways of implementing the method according to the invention, optionally one or more of the following arrangements may furthermore be used:

the region to be probed and the reference region are scanned along a first direction in space at a frequency $f_x$ and along a second direction in space at a frequency $f_y$, in order to form an image of n pixels along the first direction and m pixels along the second direction, the frequencies $f_x$ and $f_y$ being chosen such that $f_x=f_y/n$ and $f_y=f_a/m$, $f_x$ and $f_y$ being greater than $f_c$;

the medium is excited at a frequency $f_e$ and the variation in the phase of the probe beam relative to that of the reference beam is measured at this same frequency $f_e$;

knowing the distribution of the electrooptic properties of the medium, a mapping of the electric field in the medium is carried out;

an electric field of known configuration is generated in the medium so as to reveal electrooptic properties of the medium; and the medium is doped with molecules or ions etc. having electrooptic properties, or conferring electrooptic properties on the medium, so as to accentuate the electrooptic properties of the medium, if the latter is already endowed therewith, or to reveal the presence of electric fields in a medium that does not possess such properties intrinsically.

The nature of the probed media may, thanks to the invention, be highly varied. Apart from the optoelectronic components already mentioned, there may be a local distribution, for example an interface between two different dielectric media each devoid of any intrinsic electrooptic activity. The interface between the two media having individually nonelectrooptic character therefore induces a structural break in centrosymmetry near the discontinuity and the possibility of an electrooptic effect. In another example of a local distribution of the electrooptic properties, the medium is amorphous. For example, it may be a polymer matrix containing a solid solution of randomly dispersed electrooptic molecules that have been locally oriented in a noncentrosymmetric random order, (owing to the effect of an electric field locally induced by a suitable electrode or by optical fields in a configuration called an all-optical orientation, which acts locally at the focus of the orienting beams). Such local occurrences of electrooptic properties may be denoted by either of the following suggestive names: "electrooptic surfaces" (in the case of two-dimensional or quasi-two-dimensional distribution of the membrane type) or "electrooptic islands" (or voxels) in the case of inclusions of electrooptic structures exogenic to the ambient medium. For example, in this case there may be inclusions of electrooptic structures in a film of amorphous polymer devoid of intrinsic electrooptic properties (these inclusions having nanoscale or microscale dimensions, for example nanocrystals having quadratic nonlinear properties). Conversely, it is possible to create, by axial disorientation, a local defect having an electrooptic effect within an initially homogeneous electrooptic structure (as obtained by quasi-uniform orientation in an electric field in a conventional configuration of the corona needle type). In particular, the invention is useful in two symmetrical situations. Firstly, it makes it possible, when the distribution of the electrooptic properties is unknown, to reveal the spatial mapping of this a priori unknown distribution by applying an electric field with a set of simple electrodes that allows the distribution of the field within the specimen to be controlled as well as possible. Secondly, when the spatial distribution of the electrooptic properties is well known by other means (for example in the case of a technological method for the controlled formation of this distribution), the invention makes it possible to determine the mapping of the internal or external field within the distribution, the latter depending both on this a priori known distribution of the electrooptic properties, but also on the geometry of the electrodes via which an external electric field is applied. In certain intermediate cases, knowledge about both the distribution of the electric field and the electrooptic properties of the structures proves to be limited. The invention then makes it possible for the optical phase shift experienced by the incident wave probing the medium to be mapped with certainty, despite these two unknowns. To make progress in resolving the indeterminacies, a person skilled in the art will therefore propose structural and/or physical hypotheses with respect to either the structure of the electrooptic medium, or the field distribution, or a combination of the two.

BRIEF DESCRIPTION OF THE DRAWINGS

FIGS. 5a to 5f show schematically a few examples of applications of the method according to the invention.

In the various figures, the same references denote identical or similar elements.

DESCRIPTION OF PREFERRED EMBODIMENTS

One example of an embodiment of the device according to the invention is presented below in relation to FIGS. 1 to 5.

In this example, the device according to the invention is a device for the quantitative and noninvasive detection and mapping of an electric field or potential or else of their spatial and/or temporal derivatives in an optically active, and possibly structurally known, medium.

Figure 1:
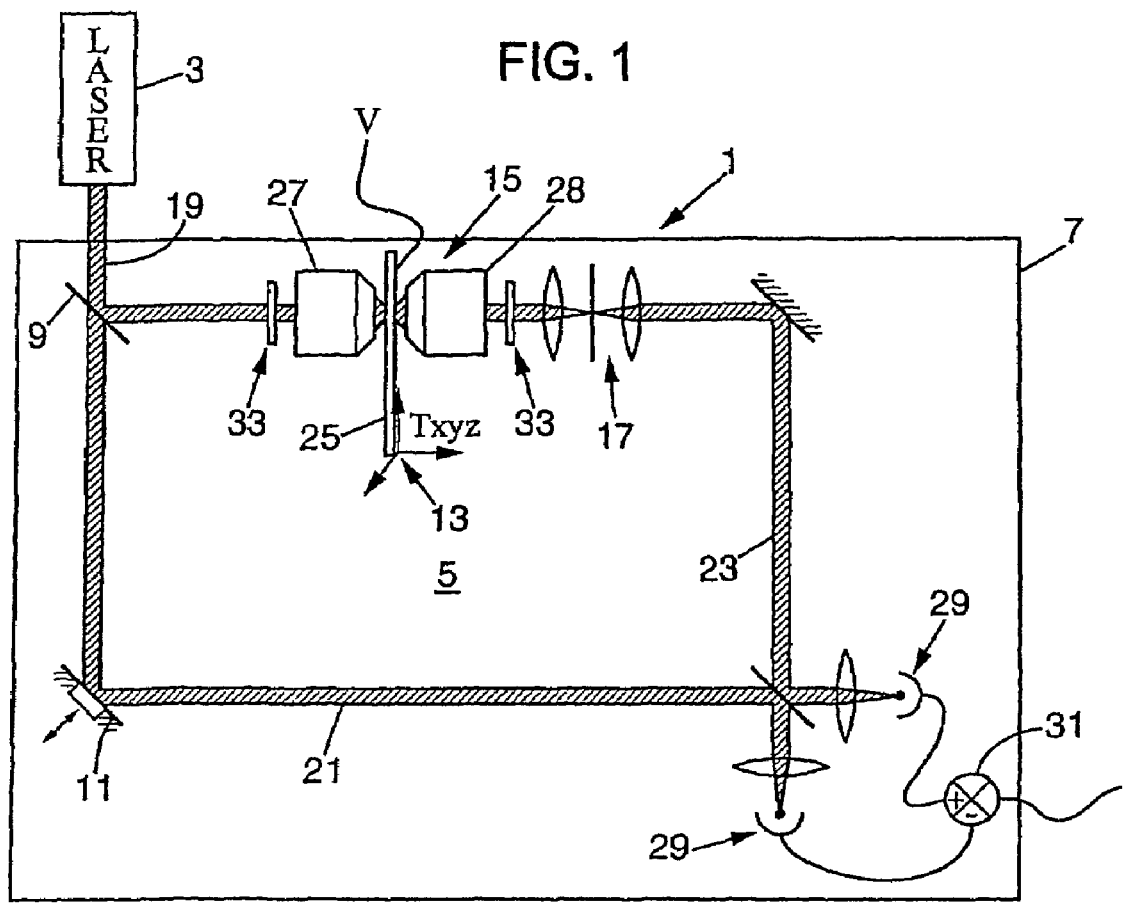
FIG. 1 is a diagram showing the principle of one example of an embodiment of a device according to the present invention.

As shown in FIG. 1, this device 1 is a microscope. It comprises an optical source 3 and an interferometer 5 consisting of means 7 for mapping the phase shift of a light beam. It thus allows the variations in the refractive index to be measured.

The optical source 3 is for example a laser. The wavelength, the power and the nature (pulsed or continuous) of this laser are, of course, tailored to the medium to be probed and more particularly to the optically active species (molecules, ions, electronic material, etc.) that reveals the electric field within this medium. For example, for an application involving the study of optoelectronic components, an He/Ne laser emitting at 632.8 nm with a power of a few milliwatts may be required for use.

The interferometer 5 comprises splitter means 9, for example means consisting of a half-wave plate and a polarizer, servocontrolled mirrors 11, a specimen holder 13, a confocal microscope 15 and optical elements 17. According to the embodiment example of the microscope shown in FIG. 1, the electric fields are detected in transmission mode. Of course, it is also within the competence of a person skilled in the art to transpose this teaching in order to carry out this detection in reflection mode.

The interferometer 5 is mounted in homodyne detection mode. The splitter means 9 split the light beam 19 emitted by the source 3 into a reference beam 21 and a probe beam 23. The quadrature between the reference beam 21 and the probe beam 23 is slaved to $\pi/2$ so as to determine the relative variation in optical path. An example of the servocontrol of the mirrors 11 is given in the doctoral thesis by P. F. Cohadon (Laboratoire Kastler-Brossel, Paris University VI, January 2000).

The probe beam 23 is focused in a region of a specimen 25 mounted in the specimen holder 13 by means of a first optic 27 of the confocal microscope 15. A second optic 28 of the confocal microscope 15 collects the light beam transmitted by the specimen 25 in this region. It should be noted that, in the case of detection in reflection mode, the reflection may optionally take place after the second optic 28. The light beam is then filtered by the optical elements 17 comprising a diaphragm that intercepts the entire signal that does not pass through the focus of the second optic 28.

The specimen 25 is moved in the probe beam 23 by a piezoelectric block that moves the specimen holder 13 in the three directions in space. The specimen 25 is thus probed volumewise. Thanks to the piezoelectric block, it is possible for the electric fields in the specimen 25 to be mapped in three dimensions.

The probe beam 23 is detected and recorded by means 7 for mapping the phase shift of the light beam. More precisely, these means comprise detectors 29 and an electronic processing and servocontrol unit 31.

The detectors 29 are ultrafast high-sensitivity photodiodes such as those described in the aforementioned doctoral thesis of P. F. Cohadon. These detectors 29 are used both for servocontrolling the relative optical path lengths of the reference beam 21 and the probe beam 23 and for recording the signal transmitted by the specimen 25.

The electronic processing and servocontrol unit 31 is a high-frequency electronic unit known to those skilled in the art.

The device 1 further includes means 33 for scanning the probe beam 23 over the specimen 25.

Figure 2:
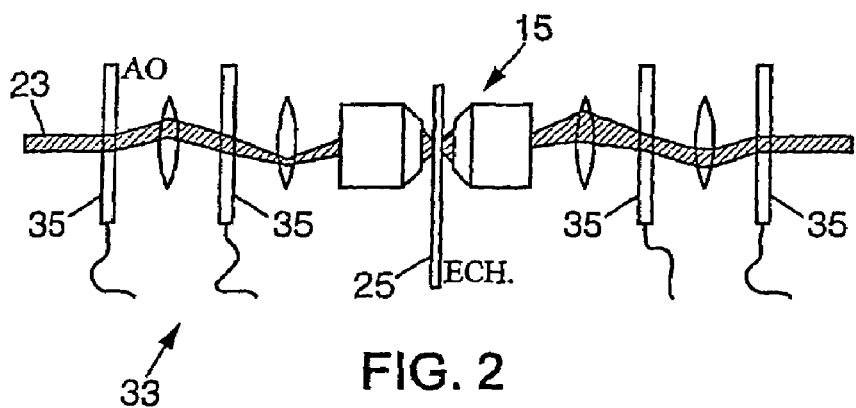
FIG. 2 shows schematically the scanning means of the device of FIG. 1.

These scanning means 33 are illustrated in greater detail in FIG. 2. Many embodiments of the scanning means 33 may of course be envisaged by those skilled in the art. Here, only one embodiment is shown. According to this embodiment, the scanning means 33 comprise four acoustooptic deflectors 35.

Two of these deflectors 35 are placed upstream of the confocal microscope 15 in order to deflect the probe beam 23. These deflectors 35 upstream of the confocal microscope are inclined so as to retain only the 1st-order of the beam parallel to the optical axis. One of these two deflectors causes the specimen 25 to be scanned with the probe beam 23 along a first direction in space, at a frequency $f_x$, which is also the acquisition frequency. The other of these two deflectors causes the specimen 25 to be scanned with the probe beam 23 along a second direction in space, at a frequency $f_y$ (see FIG. 3). An image consisting of n pixels along the first direction and m pixels along the second direction is thus formed. If the signal sampling frequency is $f_a$, the frequencies $f_x$ and $f_y$ are chosen such that $f_x = f_a/n$ and $f_y = f_a/m$, and such that both these are above the cutoff frequency $f_c$.

The other two of the four deflectors 35 are placed downstream of the confocal microscope 15 and allow the probe beam 23 to be rectified, each in one of the first and second directions in space respectively.

The scanning means 33 make it possible to modulate, at the frequency $f_x$ above the cutoff frequency $f_c$, the signal coming from the possible electric fields detected.

Figure 3:
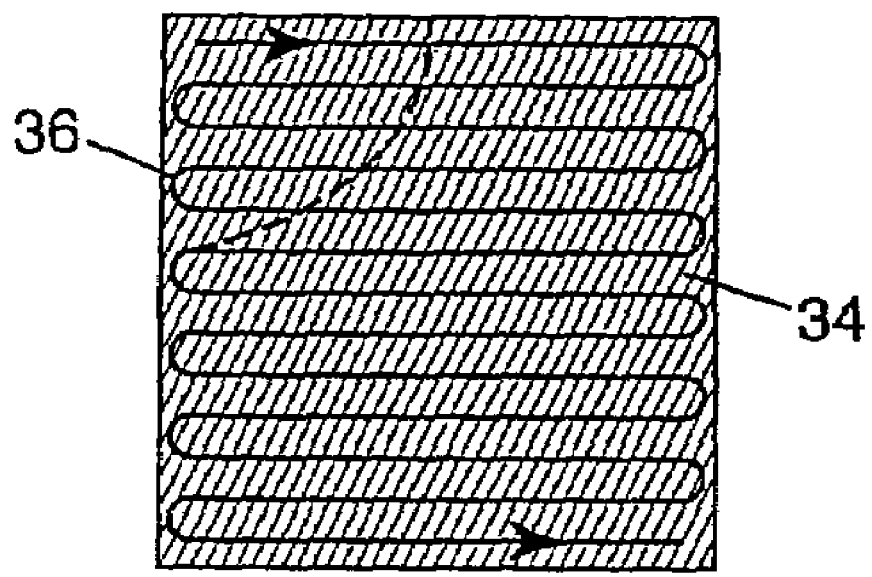
FIG. 3 shows schematically the scanning carried out by the scanning means of FIG. 2.

As illustrated in FIG. 3, the signal transmitted by the specimen 25 during the scan along the first and second directions is recorded. This scan passes via a region 34 to be probed and a reference region 36. This reference region 36 may be a region of the specimen 25 itself in which the electric fields do not vary. A reference image, that is to say an image of the phase with no potential or with a reference or rest potential, is then subtracted from the image of the signal coming from the possible electric fields detected. The image of this signal coming from the possible detected variations of the electric fields is thus displayed on a black background. The detection is therefore a synchronous detection.

The signal coming from the possible electric field detected is demodulated in the electronic processing and servocontrol unit 31 in a conventional manner.

Figure 4:
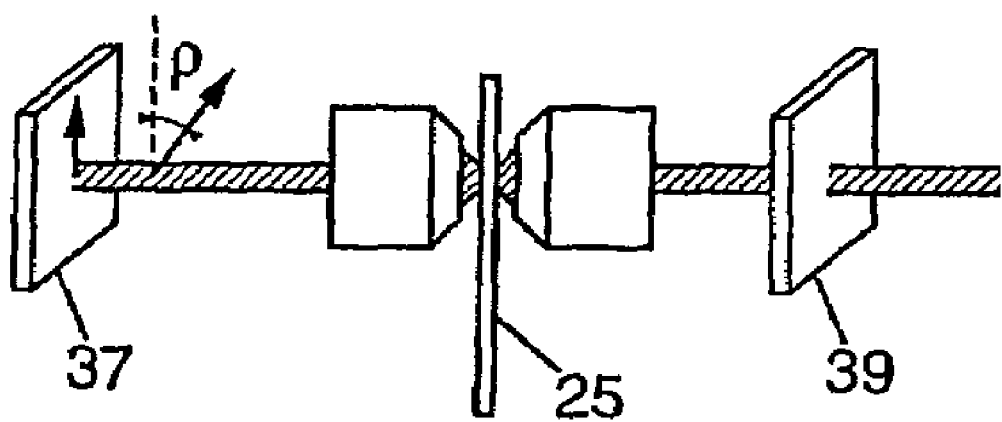
FIG. 4 shows schematically a variant of part of the device of FIGS. 1 to 3.

In another variant of the device according to the invention, shown in FIG. 4, which may be combined with the embodiment already explained, this includes means 37 for controlling the polarization of the probe beam 23. These polarization control means 37 allow the polarization state of the probe beam 23 incident on the specimen 25 to be varied in a controlled manner. For example, these are polarization control means 37 suitable for obtaining a linear polarization of the probe beam 23, the polarization angle ρ of which in the plane transverse to the propagation axis can be varied over 360°. Such polarization control means 37 may be formed by any device known to those skilled in the art for the preparation and rotation of a linear polarization state in the plane transverse to the optical axis. In particular, they may comprise a half-wave plate and/or a polarizer.

Such polarization control means 37 are placed upstream of the first optic 27. A person skilled in the art is then capable of carrying out the corrective calculations needed to switch the linear polarization state upstream of this first optic 27 to the elliptic polarization state in the specimen 25. An optional polarization analyzer 39 may be placed on the downstream side of the second optic 28, as a complement to the polarization control means 37.

The device according to the invention may be used to detect electric fields whose variations occur at a frequency below the cutoff frequency $f_c$ for servocontrolling the relative path length of the reference beam 21 and the probe beam 23. Thus, it may be used for detecting periodic or aperiodic signals that may or may not be transient and may or may not be reproducible.

The device described above may be used in many applications.

As an example, this device may be used in a method according to the invention for testing optoelectronic components.

In the present document, the term "optoelectronic component" is understood to mean an electronic, microelectronic or optronic component, or else a circuit comprising components of at least one of these types. Advantageously, these optoelectronic components exhibit an electrooptic effect, at least in part of the region to be studied and/or mapped.

More particularly, in this type of method, a reproducible periodic excitation potential is created between two electrodes. The region 34 to be probed includes at least one part of an optoelectronic component to which this potential is applied.

This type of method may be used for studying segmented media (see FIG. 5a). It therefore allows optoelectronic component fabrication processes to be characterized and validated on the micron and/or submicron scales. For example, it is thus possible to measure the resolution of optically active etched regions.

This type of method may also be used for studying electric field gradients, especially by the use of electrodes of nontrivial shape (FIG. 5b). These are for example multipolar electrodes (cf. octupolar geometry as described in the article by J. Zyss, Nonlinear Optics, Vol. 1, page 3, 1991; see also FIG. 5c) via which an electric potential is applied. An electrooptic structure of multipolar symmetry matched to that of the electrodes allows the derivatives of the field to be revealed, for example the second derivative of the field at the center of a set of octupolar electrodes, as depicted in FIG. 5c, the field and its first derivative being made zero by the symmetry at the center of the orientation microcell shown diagrammatically therein. It is thus possible, thanks to the method according to the invention, to map electric field gradients or curvatures in optically active regions. These field maps may be compared with calculations for the validation and refining of models or, on the contrary, they make it possible to search for field configurations whose particular properties cannot be easily calculated.

This type of method may also be used for studying multipolar fields (see FIG. 5c). In this case, the potential is applied via at least one electrode with multipolar symmetry. Configurations of electrodes with multipolar symmetry allow multipolar field structures to be examined. Such multipolar field structures make it possible, for example, to understand the orientational distribution of molecules under the influence of these multipolar fields.

In another application of the method according to the invention, the propagation of pulses in a conductor (a wire, integrated circuit, optoelectronic component, etc.) may be studied. This conductor is then placed in an optically active medium. By exposing the medium to ultrashort pulses, it is possible to examine, by frequency analysis of the propagation of these pulses in the conductor, ultrashort transient regimes and information about the ohmic resistance of the conductor (see FIG. 5d).

Another application of the method according to the invention is in the study of phenomena such as field transfer, spatial overlap, etc. In optoelectronic components, the field applied between electrodes does not always have a simple form (see FIG. 5e). In particular, field transfer and spatial overlap problems may occur, both in the static case (poling of the active layer of the component) and in the dynamic case (modulation field). By mapping the electric fields using the method according to the invention, it is possible to optimize the shape and structure of these components, for example so as to result in reduction in the control voltage.

Another application of the method according to the invention is in the study of fractal aggregates, particularly percolation in these aggregates. In the region 34 to be probed there may be at least part of a fractal aggregate (see FIG. 5f).

There are also particularly useful applications of the device and the method according to the invention in the field of biology. In this case, the region 34 to be probed includes at least one part of a natural or artificial biological medium. For example, the region 34 to be probed includes at least one part of a natural or artificial biological membrane.

Thus, one application of the method according to the invention is the study of biomimetic systems, for example the diffusion of molecular species through artificial membranes. Modifications of these membranes, due to phenomena of various types (chemical, biochemical, electrical, electromagnetic radiation, etc.), may be detected thanks to the device according to the invention. This type of application may extend to the study of microfluidic systems, capsules, vesicles, etc.

The method according to the invention may also be used to study biological systems, such as neurons, animal or plant cells, etc.

For the purpose of studying healthy neurons, the region 34 to be probed includes at least one part of a neuron or of a neural network and the device according to the invention allows the propagation of neural and/or interneuronal electrical signals, the origin of these signals, etc. to be determined. The device according to the invention in this case advantageously replaces the "patch-clamp" technique for which, for example for a field of observation measuring $10 \times 10$ μm$^2$, several tens of thousands of electrodes, or more, would have been necessary in order to obtain an equivalent mapping. The device according to the invention also overcomes contact problems, stearic hindrance problems, etc.

The device according to the invention also can be used to study disturbed or pathological neurons, sclerosed neurons, degenerated neurons, etc.

Thanks to the device according to the invention, it is also possible to observe small-scale electrical phenomena, such as overvoltage phenomena or those occurring in oxidation-reduction chemical reactions, in chemical reactors possibly on a nanoscale, in micelles, in humic-clay complexes, etc. The region 34 to be probed therefore constitutes at least one part of a chemical medium.

In certain cases, whether in electronics or in biology, the medium must be doped with electrooptic molecules or ions so as to accentuate the electrooptic properties of the medium and/or to allow electric fields to be observed in media that do not have such properties.

As an example of electrooptic molecules, the following molecules may be mentioned:

the molecule "DR1" (Dispersed Red 1) is well known to those skilled in the art. It is used more for studying optoelectronic components and biomimetic systems;

the molecule "Crystal Violet" is also well known to those skilled in the art. It constitutes an example of an octupole. It is sensitive to successive gradients of the electric field and not to the electric field itself. The method according to the present invention is not limited to detecting electric fields with $2^{nd}$-order nonlinearities since higher-order nonlinearities may be used; and molecules derived from phthalocyanine by peripheral substitution with electron donor and accepter groups in a noncentrosymmetric geometry are also known to those skilled in the art. They can be used for studying biological systems. Many other molecules may be used. In particular, molecules having different shapes from those indicated above or derivatives of these molecules may be used.

The invention claimed is:

1. A device for noninvasive detection of the properties of a medium by interferometry, this device comprising:

an optical source for illuminating at least one region of the medium to be probed, with a light beam whose path defines an optical axis;

means for measuring variations in the phase of the light beam during its passage through the region to be probed, these measurement means comprising an interferometer for splitting the light beam into a reference beam and a probe beam, and means for servocontrolling the path lengths of the reference beam and of the probe beam, in this interferometer the the respective path lengths of the reference beam and of the probe beam being servocontrolled up to a cutoff frequency $f_c$ and having a signal sampling frequency $f_a$, wherein said device further includes means for scanning, with the probe beam, the region to be probed and a reference region with an image acquisition frequency f for images recorded by the means for measuring the variations in the phase of the light beam above the cutoff frequency $f_c$.

2. The device as claimed in claim 1, wherein the means for scanning scan the region to be probed and the reference region along a first direction in space at a frequency $f_x$ and along a second direction in space at a frequency $f_y$, in order to form an image of n pixels along the first direction and m pixels along the second direction, the frequencies $f_x$ and $f_y$ being chosen such that $f_x=f_y/n$, and $f_y=f_a/m$, $f_x$ and $f_y$ being greater than $f_c$.

3. The device as claimed in claim 1, wherein the means for measuring the variations in the phase of the light beam comprise a confocal microscope in which the region to be probed is placed in a manner suitable for forming an image of a plane of the region to be probed.

4. The device as claimed in claim 1, comprising means for moving the medium, along the three directions in space, while maintaining the medium in contact with the probe beam.

5. The device as claimed in claim 1, wherein the means for scanning comprise four acoustooptic deflectors, two for deflecting the light beam, upstream of the confocal microscope, each in one of the first and second directions in space respectively, and two for rectifying the light beam, each in one of the first and second directions in space respectively, downstream of the confocal microscope.

6. The device as claimed in claim 5, wherein at least one acoustooptic deflector, downstream of the confocal microscope is set so as to make the 0th-order of the light beam inclined to the optical axis and to retain the paraxial 1st-order.

7. The device as claimed in claim 1, which further includes, upstream of the confocal microscope, means for controlling the polarization of the probe beam incident on the region to be probed.

8. A method of noninvasively detecting the properties of a medium by interferometry, comprising the steps of:

illuminating at least one region of the medium to be probed with an optical source that generates a light beam, the path of which defines an optical axis;

splitting the light beam into a reference beam and a probe beam by using an interferometer and measuring phase shift between the reference beam and the probe beam after the latter has passed through the region to be probed;

detecting and recording the probe beam with means for measuring the phase shift of the light beam;

servocontrolling respective path lengths of the reference beam and the probe beam by using means for performing photodetection; and acquiring images corresponding to the measurement of the phase shift at various points in the region to be probed, with the photodetection means, at a signal sampling frequency $f_a$ above a cutoff frequency $f_c$ for servocontrolling the respective path lengths of the reference beam and the probe beam, wherein the method further comprises the step of scanning the region to be probed and a reference region with the probe beam at an image acquisition frequency f for images recorded by means for measuring the variations in the phase of the light beam above the cutoff frequency $f_c$.

9. The method as claimed in claim 8, wherein the region to be probed and the reference region are scanned along a first direction in space at a frequency $f_x$ and along a second direction in space at a frequency $f_y$, in order to form an image of n pixels along the first direction and m pixels along the second direction, the frequencies $f_x$ and $f_y$ being chosen such that $f_x=f_y/n$ and $f_y=f_a/m$, $f_x$ and $f_y$ being greater than $f_c$.

10. The method as claimed in claim 8, wherein the region to be probed is placed in a confocal microscope in a manner suitable for forming an image of one plane of the region to be probed.

11. The method as claimed in claim 8, wherein the medium is moved, along the three directions in space, while maintaining the medium in contact with the probe beam.

12. The method as claimed in claim 8, wherein the medium is excited at a frequency $f_e$ and the variation in the phase of the probe beam relative to that of the reference beam is measured at this same frequency $f_e$.

13. The method as claimed in claim 8, wherein the $0^{th}$-order of the light beam is deflected relative to the optical axis by means of at least one acoustooptic deflector, downstream of the confocal microscope, and the paraxial $1^{st}$-order is retained.

14. The method as claimed in claim 8, wherein the region to be probed includes at least one part of a optoelectronic component to which a potential is applied.

15. The method as claimed in claim 14, wherein the potential is applied via at least one electrode, the shape of which is suitable for creating a electric field gradient.

16. The method as claimed in claim 14, wherein the potential is applied via at least one multipolar electrode.

17. The method as claimed in claim 14, wherein the optoelectronic component is placed in an optically active medium.

18. The method as claimed in claim 14, wherein the propagation of a electrical pulse in the optoelectronic component is studied.

19. The method as claimed in claim 8, wherein the region to be probed includes at least one peat of a fractal aggregate.

20. The method as claimed in claim 8, wherein the region to be probed includes at least one part of a biological medium.

21. The method as claimed in claim 20, wherein the region to be probed includes at least one part of a biological membrane.

22. The method as claimed in claim 20, wherein the region to be probed includes at least one part of a neuron or of a neural network.

23. The method as claimed in claim 8, wherein the region to be probed includes at least one part of an artificial membrane.

24. The method as claimed in claim 8, wherein the region to be probed constitutes at least one part of a chemical medium.

25. The method as claimed in claim 8, wherein the medium is doped with molecules or ions having electrooptic properties, or conferring electrooptic properties on the medium, so as to accentuate the electrooptic properties of the medium, if said medium is already endowed therewith, or to reveal the presence of electric fields in a medium that does not possess such properties intrinsically.

26. The method as claimed in claim 25, wherein, knowing the distribution of the electrooptic properties of the medium, a mapping of the electric field in the medium is carried out.

27. The method as claimed in claim 8, wherein an electric field of known configuration is generated in the medium so as to reveal electrooptic properties of the medium.

* * * * *